US011399965B2

(12) United States Patent
Dewey et al.

(10) Patent No.: US 11,399,965 B2
(45) Date of Patent: Aug. 2, 2022

(54) SPINAL IMPLANT SYSTEM AND METHODS OF USE

(71) Applicant: Warsaw Orthopedic, Inc., Warsaw, IN (US)

(72) Inventors: Jonathan M. Dewey, Memphis, TN (US); Fuad N. Mefleh, Thornton, CO (US); Cathlene Donaldson, Chicago, IL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 491 days.

(21) Appl. No.: 16/564,290

(22) Filed: Sep. 9, 2019

(65) Prior Publication Data
US 2021/0068986 A1    Mar. 11, 2021

(51) Int. Cl.
*A61F 2/46*  (2006.01)
*A61F 2/44*  (2006.01)
(Continued)

(52) U.S. Cl.
CPC ............ *A61F 2/4684* (2013.01); *A61B 34/10* (2016.02); *A61B 34/25* (2016.02); *A61F 2/44* (2013.01);
(Continued)

(58) Field of Classification Search
CPC ............ A61B 90/37; A61B 2034/2055; A61B 2034/102; A61B 2090/3966; A61B 2090/364; A61F 2/44; A61F 2/4684
See application file for complete search history.

(56) References Cited

U.S. PATENT DOCUMENTS

| 5,885,286 A | 3/1999 | Sherman et al. |
| 6,280,442 B1 | 8/2001 | Barker et al. |

(Continued)

FOREIGN PATENT DOCUMENTS

| KR | 101049507 B1 | 7/2011 |
| WO | 2018193317 A1 | 10/2018 |

OTHER PUBLICATIONS

ISA/KR International Application Division, Korean Property Office Republic of Korea, Written Opinion of the International Searching Authority, International Search Report, International application No. PCT/US2020/049304 dated Dec. 16, 2020.

*Primary Examiner* — David W Bates
(74) *Attorney, Agent, or Firm* — Sorell, Lenna & Schmidt, LLP

(57) ABSTRACT

A surgical system includes a trial connected with a first image guide oriented relative to a sensor to communicate a signal representative of the trial relative to a patient anatomy. A tracking device includes the sensor and communicates with a processor to generate a storable image of the trial relative to the patient anatomy for display from a monitor. A spinal implant is connected with a second image guide oriented relative to the sensor to communicate a signal representative of the spinal implant relative to the patient anatomy. The sensor receives the signal of the second image guide and communicates with the processor to generate an image of the spinal implant in real time for display from the monitor in a configuration to align the spinal implant in real time with the stored image of the trial. In some embodiments, methods, spinal constructs, implants and surgical instruments are disclosed.

20 Claims, 15 Drawing Sheets

(51) Int. Cl.
  *A61B 34/20*    (2016.01)
  *A61B 90/00*    (2016.01)
  *A61B 34/10*    (2016.01)
  *A61B 34/00*    (2016.01)
  *A61B 17/70*    (2006.01)

(52) U.S. Cl.
  CPC ......... *A61F 2/4611* (2013.01); *A61B 17/7071* (2013.01); *A61B 34/20* (2016.02); *A61B 2034/102* (2016.02); *A61B 2034/107* (2016.02); *A61B 2034/2055* (2016.02); *A61B 2090/3966* (2016.02); *A61B 2090/3983* (2016.02); *A61F 2002/4658* (2013.01)

(56) References Cited

U.S. PATENT DOCUMENTS

| | | |
|---|---|---|
| 6,485,491 B1 | 11/2002 | Farris et al. |
| 6,565,566 B1 | 5/2003 | Wagner et al. |
| 8,034,089 B2 | 10/2011 | Matthis et al. |
| 8,097,025 B2 | 1/2012 | Hawkes et al. |
| 8,167,910 B2 | 5/2012 | Nilsson |
| 8,197,518 B2 | 6/2012 | Hammill, Sr. et al. |
| 8,298,265 B2 | 10/2012 | Purcell et al. |
| 8,298,275 B2 | 10/2012 | Rezach et al. |
| 9,084,634 B1 | 7/2015 | Lab et al. |
| 9,510,771 B1 * | 12/2016 | Finley .................... A61B 34/20 |
| 11,000,382 B1 * | 5/2021 | Cole .................... A61B 5/4528 |
| 2007/0093826 A1 | 4/2007 | Hawkes et al. |
| 2007/0167741 A1 * | 7/2007 | Sherman ................ A61B 90/36 600/424 |
| 2007/0270839 A1 | 11/2007 | Jeon et al. |
| 2008/0161859 A1 | 7/2008 | Nilsson |
| 2009/0248075 A1 | 10/2009 | Ogilvie et al. |
| 2010/0036433 A1 | 2/2010 | Jackson |
| 2010/0076305 A1 * | 3/2010 | Maier-Hein ............ A61B 6/12 600/426 |
| 2011/0093021 A1 | 4/2011 | Fanger et al. |
| 2011/0098755 A1 | 4/2011 | Jackson et al. |
| 2011/0306873 A1 | 12/2011 | Shenai et al. |
| 2012/0041490 A1 | 2/2012 | Jacob et al. |
| 2015/0100129 A1 * | 4/2015 | Waugh .................. A61F 2/4611 623/17.16 |
| 2015/0257846 A1 * | 9/2015 | Kubiak .................. A61B 6/485 600/407 |
| 2015/0282797 A1 * | 10/2015 | O'Neil .................. A61B 1/3135 606/279 |
| 2015/0342757 A1 | 12/2015 | Lomeli et al. |
| 2016/0100909 A1 * | 4/2016 | Wollowick ............. A61B 34/20 600/424 |
| 2016/0175108 A1 * | 6/2016 | Howard .................. A61F 2/442 623/17.14 |
| 2016/0310218 A1 * | 10/2016 | Ruckel .................... A61B 34/20 |
| 2018/0116824 A1 * | 5/2018 | Dewey .................... A61F 2/442 |
| 2019/0133693 A1 * | 5/2019 | Mahfouz .............. A61B 6/5229 |
| 2019/0298546 A1 * | 10/2019 | Dewey .................... A61F 2/4684 |
| 2020/0093613 A1 * | 3/2020 | Arramon ............. A61F 2/30771 |
| 2020/0297513 A1 * | 9/2020 | Zellmer ................ A61B 34/25 |
| 2020/0323654 A1 * | 10/2020 | Marrapode ........... A61F 2/4455 |
| 2021/0007811 A1 * | 1/2021 | Troxell .................. A61B 90/50 |
| 2021/0068985 A1 * | 3/2021 | Dewey .................. A61B 34/20 |

* cited by examiner

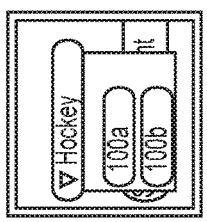
FIG. 13
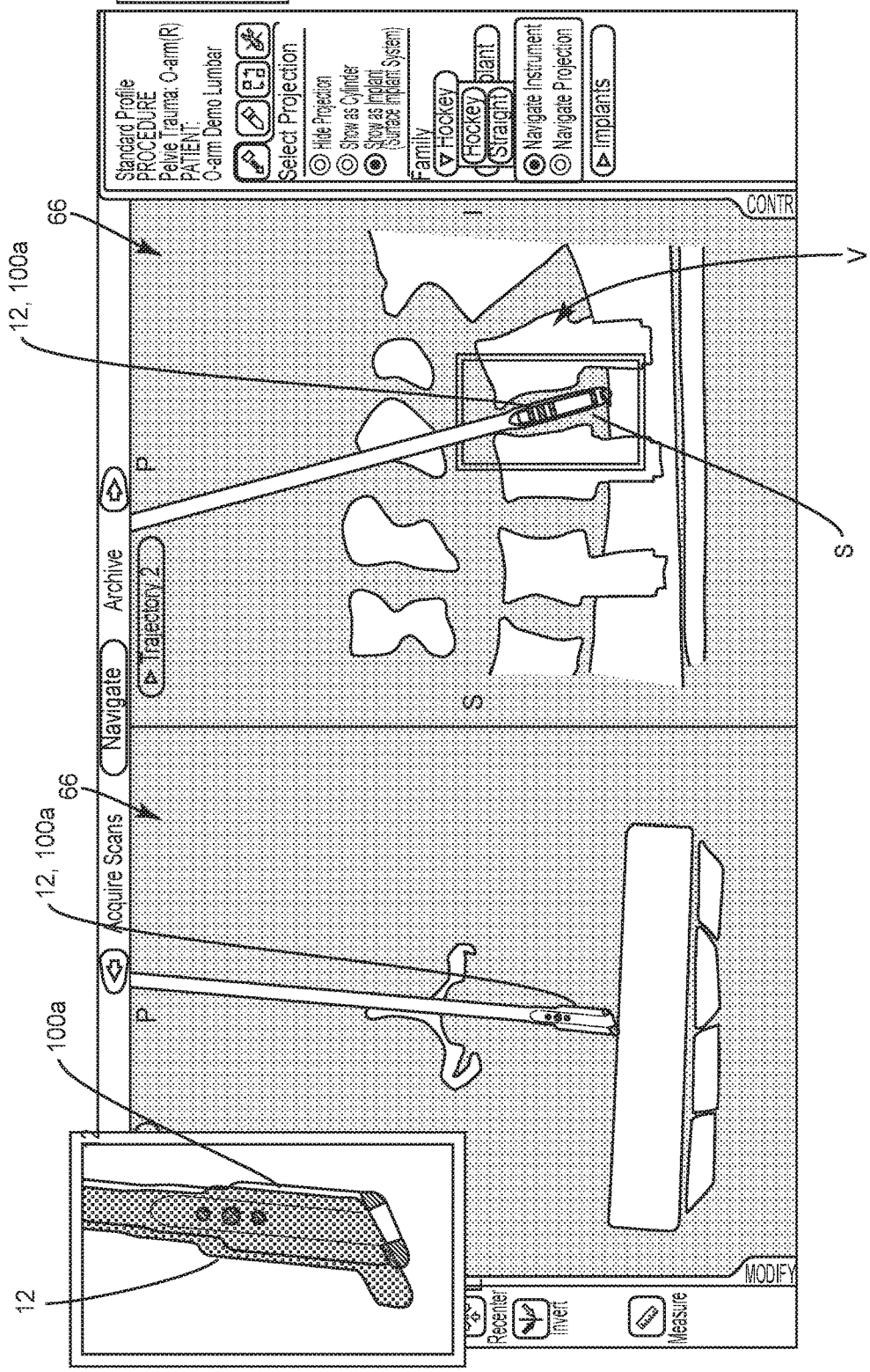
FIG. 14
FIG. 15

SPINAL IMPLANT SYSTEM AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, surgical instruments are employed, for example, to facilitate surgical preparation, manipulation of tissue and delivering implants to a surgical site. This disclosure describes an improvement over these prior technologies.

SUMMARY

In one embodiment, a surgical system is provided. The surgical system includes a trial connected with a first image guide oriented relative to a sensor to communicate a signal representative of the trial relative to a patient anatomy. A tracking device includes the sensor and communicates with a processor to generate a storable image of the trial relative to the patient anatomy for display from a monitor. A spinal implant is connected with a second image guide oriented relative to the sensor to communicate a signal representative of the spinal implant relative to the patient anatomy. The sensor receives the signal of the second image guide and communicates with the processor to generate an image of the spinal implant in real time for display from the monitor in a configuration to align the spinal implant in real time with the stored image of the trial. In some embodiments, methods, spinal constructs, implants and surgical instruments are disclosed.

In one embodiment, a system is provided, which includes a tangible storage device comprising computer-readable instructions. An image guide is oriented relative to a sensor for positional tracking of one or more trials, one or more spinal implants and/or a patient anatomy. A processor, executes the instructions in operation of the system for: imaging at least one trial with the patient anatomy; acquiring data points representative of an image of the at least one trial selectively positioned relative to the patient anatomy; displaying the image from a computer monitor; imaging at least one spinal implant with the patient anatomy; and aligning the at least one spinal implant with the image via a display from the computer monitor.

In one embodiment, the system includes a tangible storage device comprising computer-readable instructions. An image guide is oriented relative to a sensor for positional tracking of one or more trials, one or more spinal implants and/or a patient anatomy. A processor, executes the instructions in operation of the system for: imaging a first trial disposed with vertebral tissue, the first trial having a navigation component generating a signal representative of a position of the first trial relative to the vertebral tissue; acquiring data points representative of an image of the first trial selectively positioned with a lateral portion of vertebral tissue; removing the first trial from the vertebral tissue and displaying the image from a computer monitor; imaging a second trial disposed with the vertebral tissue, the second trial having a navigation component generating a signal representative of a position of the second trial relative to the vertebral tissue; acquiring data points representative of an image of the second trial selectively positioned with a contra-lateral portion of the vertebral tissue; removing the second trial from the vertebral tissue and displaying the image of the second trial from the computer monitor; and aligning a first spinal implant with the image of the first trial via a display from the computer monitor and aligning a second spinal implant with the image of the second trial via a display from the computer monitor.

BRIEF DESCRIPTION OF THE DRAWINGS

The present disclosure will become more readily apparent from the specific description accompanied by the following drawings, in which:

FIG. 13 is a graphical representation of a computer display of components of one embodiment of a surgical system in accordance with the principles of the present disclosure disposed with vertebrae;

FIG. 14 is a graphical representation of a computer display of components of one embodiment of a surgical system in accordance with the principles of the present disclosure disposed with vertebrae;

FIG. 15 is a graphical representation of a computer display of components of one embodiment of a surgical system in accordance with the principles of the present disclosure disposed with vertebrae;

DETAILED DESCRIPTION

Figure 1:
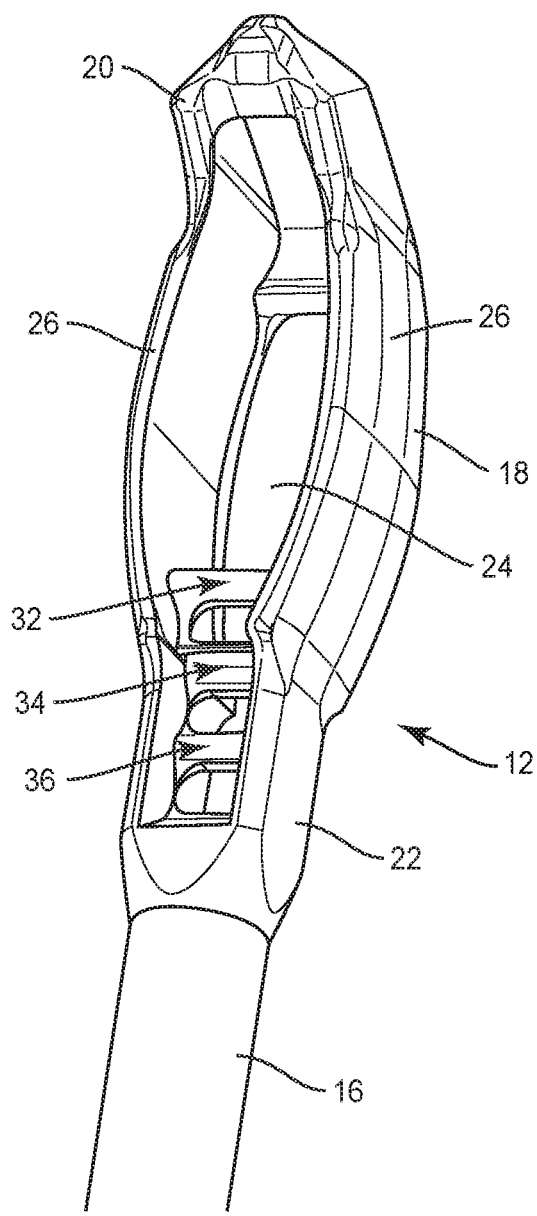
FIG. 1 is a break away perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises a method utilizing a saved image for navigated spine surgeries. In some embodiments, the systems and methods of the present disclosure comprise surgical navigation and medical devices including surgical instruments and implants that are employed with a surgical treatment, as described herein, for example, with a cervical, thoracic, lumbar and/or sacral region of a spine.

In some embodiments, the present surgical system includes images of trials and/or implants for surgical planning and performing surgical procedures. In some embodiments, the present surgical system is employed with methods that allow a surgeon to determine a size and/or configuration of an implant by projecting an image of a spinal implant and/or a surgical trial instrument in a vertebral space from a computer display employing surgical navigation.

In some embodiments, the present surgical system includes one or more trial instruments employed with methods for connection with an image guide oriented relative to a sensor to communicate a signal representative of the trial instrument relative to a patient anatomy. In some embodiments, the trial instrument includes indicia displayable from a monitor to represent orientation of the trial instrument relative to the patient anatomy. In some embodiments, the indicia includes one or more radiopaque markers disposed adjacent a distal end of the trial instrument. In some embodiments, the trial instrument includes indicia displayable from the monitor to represent a size of the spinal implant. In some embodiments, the indicia includes axial indicia, for example, one or more fins. In some embodiments, the indicia includes lateral indicia, for example, one or more axial oriented columns. In some embodiments, the columns include a distal column, an intermediate column and a proximal column. In some embodiments, the intermediate column has a diameter different than a diameter of the distal column and a diameter of the proximal column.

In some embodiments, the present surgical system is employed with methods for viewing a vertebral space axially and/or laterally to determine a size and/or configuration of an implant. In some embodiments, the systems and methods of the present disclosure facilitate determining a cross section and/or height of the vertebral space to calculate a size and/or configuration of the implant.

In some embodiments, the present surgical system is employed with methods including the step of selecting an implant strategy by selecting a size and/or configuration of an implant from a drop-down menu of a computer display that shows choices of spinal implants. In some embodiments, the present surgical system is employed with methods including the step of delivering a trial instrument according to an implant strategy. In some embodiments, the present surgical system is employed with methods including the step of adjusting a trial instrument and/or inserting various sizes of trial instruments to determine a size and/or configuration of a spinal implant. In some embodiments, the present surgical system includes a trial instrument that is imaged via communication of a navigation component and a CT-scan of a surgical navigation system. In some embodiments, the present surgical system is employed with methods including the step of acquiring data points acquired by a navigation system and displaying the data points on a monitor representing an image of the trial instrument. In some embodiments, the present surgical system includes a computer that provides a graphical user interface for adjusting the size and/or configuration of the image. In some embodiments, the method includes the step of removing the trial instrument.

In some embodiments, the present surgical system is employed with methods including the step of selecting spinal implants via a graphical user interface having a drop-down menu. In some embodiments, a surgeon selects an image of a sample spinal implant from the drop-down menu to overlay onto an image of a trial instrument. In some embodiments, parameters for a spinal implant to be implanted are calculated by a computer and are compared with the overlay image of the spinal implant to determine the final parameters for the spinal implant to be implanted. In some embodiments, the image of the trial instrument and the overlay image of the spinal implant is captured and saved with a database of a computer.

In some embodiments, the present surgical system and methods preserve the image captured such that the image position, size and/or configuration continue to be displayed from a computer monitor after a trial instrument is removed from a vertebral space, and/or the image is saved in a database memory of a computer and displayed from the computer monitor upon insertion of the spinal implant with the vertebral space. In some embodiments, the present surgical system is employed with methods including the step of inserting a spinal implant with the vertebral space and a previously captured image of the trial instrument is displayed from the computer monitor and utilized to guide and/or align a spinal implant with the image and the vertebral space, as described herein. In some embodiments, the method includes the step of manipulating the spinal implant for alignment with the data points represented by the image. In some embodiments, this configuration allows a surgeon to track more than one implant and/or active surgical instrument at a time.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
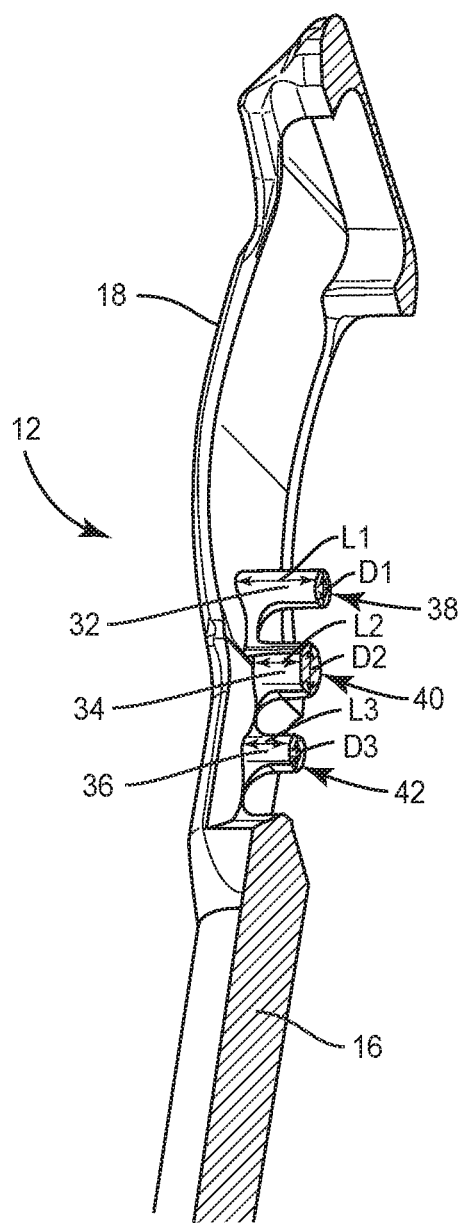
FIG. 2 is a cutaway view of the components shown in FIG. 1.
Figure 3:
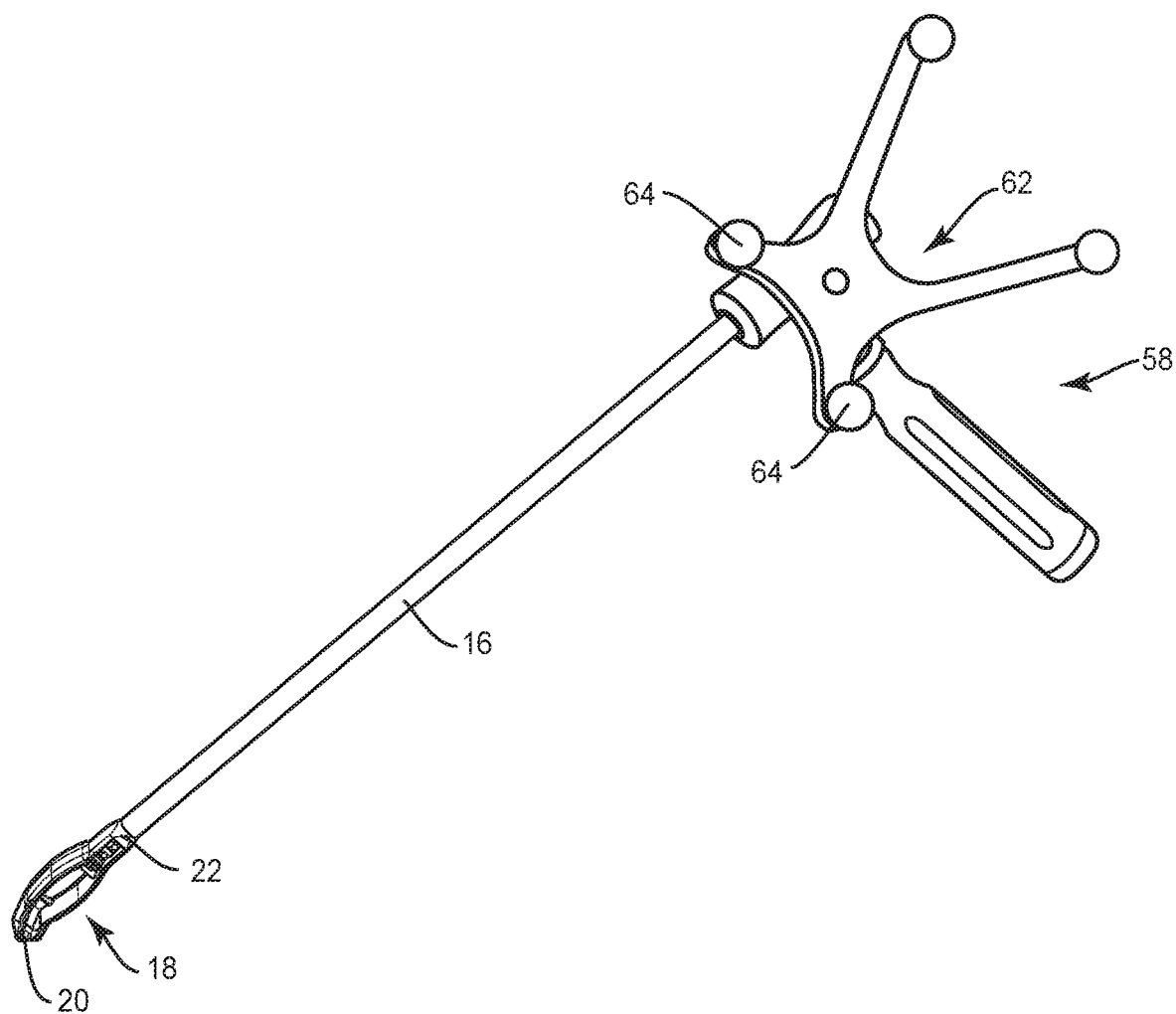
FIG. 3 is a side view of components of one embodiment of a surgical system in accordance with the principles of the present disclosure.

The following discussion includes a description of a surgical system including surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with one or more components of one or more spinal constructs, which may include spinal implants, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine. In some embodiments, the spinal constructs can be attached with vertebrae in a revision surgery to manipulate tissue and/or correct a spinal disorder, as described herein.

Surgical system 10 includes a trial instrument 12, which is employed with a surgical navigation system 14, as described herein, and one or a plurality of surgical instruments for manipulating vertebral tissue, and for delivering and introducing components of spinal constructs for engagement with the vertebral tissue. For example, trial instrument 12 is utilized to determine a size, configuration and/or positioning relative to vertebral tissue of a selected spinal implant 100, as described herein. Trial instrument 12 includes an image guide, for example, a navigation component 58, as shown in FIG. 3, which communicates with surgical navigation system 14. Navigation component 58 communicates with surgical navigation system 14 to measure, sample, capture and/or identify sizing, configuration and/or positional data points of trial instrument 12 relative to vertebral tissue for generating an image of trial instrument 12 for display from a computer monitor, as described herein. See, for example, similar surgical navigation components, imaging and their use as described in U.S. Pat. Nos. 6,021,343, 6,725,080, 6,796,988, 6,940,941, 7,001,045, 7,106,825, 7,108,421, 7,188,998 and 8,842,893, the entire contents of each of these references being incorporated by reference herein. In some embodiments, trial instrument 12 is delivered along a surgical pathway, as described herein, and used to distract one or more intervertebral spaces and apply appropriate tension in the intervertebral space allowing for decompression.

Trial instrument 12 includes a shaft 16 and a body 18 extending from shaft 16, as shown in FIGS. 1 and 2. Body 18 extends between a proximal end 20 and a distal end 22, as shown in FIG. 3. Body 18 includes a surface 24 and walls 26 extending about surface 24, as shown in FIG. 1. Body 18 includes fins 32, 34, 36 extending axially from surface 24 and laterally across body 18 between walls 26. Fin 34 is disposed intermediate to fins 32, 36. In some embodiments, fins 32, 34, 36 may be disposed at alternate orientations, relative to body 18, for example, transverse, perpendicular and/or other angular orientations such as acute or obtuse, co-axial and/or may be offset or staggered. In some embodiments, fins 32, 34, 36 are disposed at orientations relative to body 18 to convey information relating to size, configuration, positioning and/or trajectory, as described herein, to a surgeon. See, for example, the embodiments and disclosure of systems and methods including spinal implants having indicia, markers and/or columns, shown and described in commonly owned and assigned U.S. patent application Ser. No. 15/941,489 filed Mar. 30, 2018, the entire contents of which being incorporated herein by reference.

Fins 32, 34, 36 each include a cross section extending between walls 26, as shown in FIG. 2. The cross section of fins 32, 34, 36 is substantially circular defining columns 38, 40, 42, respectively. Columns 38, 40, 42 facilitate determining a length of spinal implant 100, for example, short, medium or long, as described herein. In some embodiments, column 38 includes a length L1, column 40 includes a length L2 and column 42 includes a length L3. Lengths L1, L2, L3 are varied to indicate, for example, if trial instrument 12 is small, medium or large prior to insertion into a vertebral space. Column 38 includes a diameter D1, column 40 includes a diameter D2 and column 42 includes a diameter D3. The diameter of each column 38, 40, 42 indicates a size and/or configuration of trial instrument 12 to facilitate determining a size and/or configuration of spinal implant 100. For example, diameter D2 is larger than diameter D1 and diameter D3. Column 38 includes a length L1, column 40 includes a length L2 and column 42 includes a length L3. In some embodiments, length L1 is longer than lengths L2, L3. In some embodiments, length L3 is shorter than lengths L1, L2. In some embodiments, columns 38, 40, 42 may include various cross section configurations, for example, arcuate, cylindrical, oblong, rectangular, polygonal, undulating, irregular, uniform, non-uniform, consistent, variable, U-shape and/or any other configuration that facilitates communicating size, configuration, positioning and/or trajectory to the surgeon.

Body 18 is selectively, precisely and/or accurately connected with shaft 16 such that body 18 extends a selected distance from shaft 16 in connection with surgical navigation and for generating an image of trial instrument 12 for display from a computer monitor, as described herein. Body 18 extends a selected distance from and is fixed with shaft 16 in connection with image guidance to provide size, configuration and/or position of body 18 with vertebral tissue. Distal end 22 extends a distance measured from a proximal most end surface of shaft 16 in connection with image guidance, as described herein, to dispose body 18 relative to and/or extending from shaft 16. In some embodiments, this configuration provides indicia of the size, type and/or position of body 18 relative to shaft 16 and/or vertebral tissue.

Body 18 includes indicia, for example, radiopaque markers located on various points on body 18. For example, the markers can include fins 32, 34, 36 and/or columns 38, 40, 42 and/or proximal end 20. In some embodiments, the markers facilitate viewing and/or identification of the size, configuration, orientation and/or positioning of trial instrument 12 relative to vertebral tissue under x-ray, fluoroscopy, CT or other imaging techniques by surgical navigation system 14, as described herein. The generated image of trial instrument 12 is displayed from monitor 66 and can include the markers within the vertebral space. In some embodiments, a processor of a computer 65 generates an alternate trial image having an alternate size and/or configuration relative to the image of trial instrument 12 for display from monitor 66 with the image of trial instrument 12.

In some embodiments, the generated image of trial instrument 12 is saved to a tangible storage device of computer 65 having computer-readable instructions. The generated image of trial instrument 12 is retrievable in connection with formulating an implant strategy. The image of trial instrument 12 is utilized to guide and/or align a selected spinal implant 100 into position with the vertebral space, as described herein. During a surgical procedure, spinal implant 100 is tracked in real time and displayed on monitor 66. Spinal implant 100 is tracked relative to the generated image of trial instrument 12.

Figure 5:
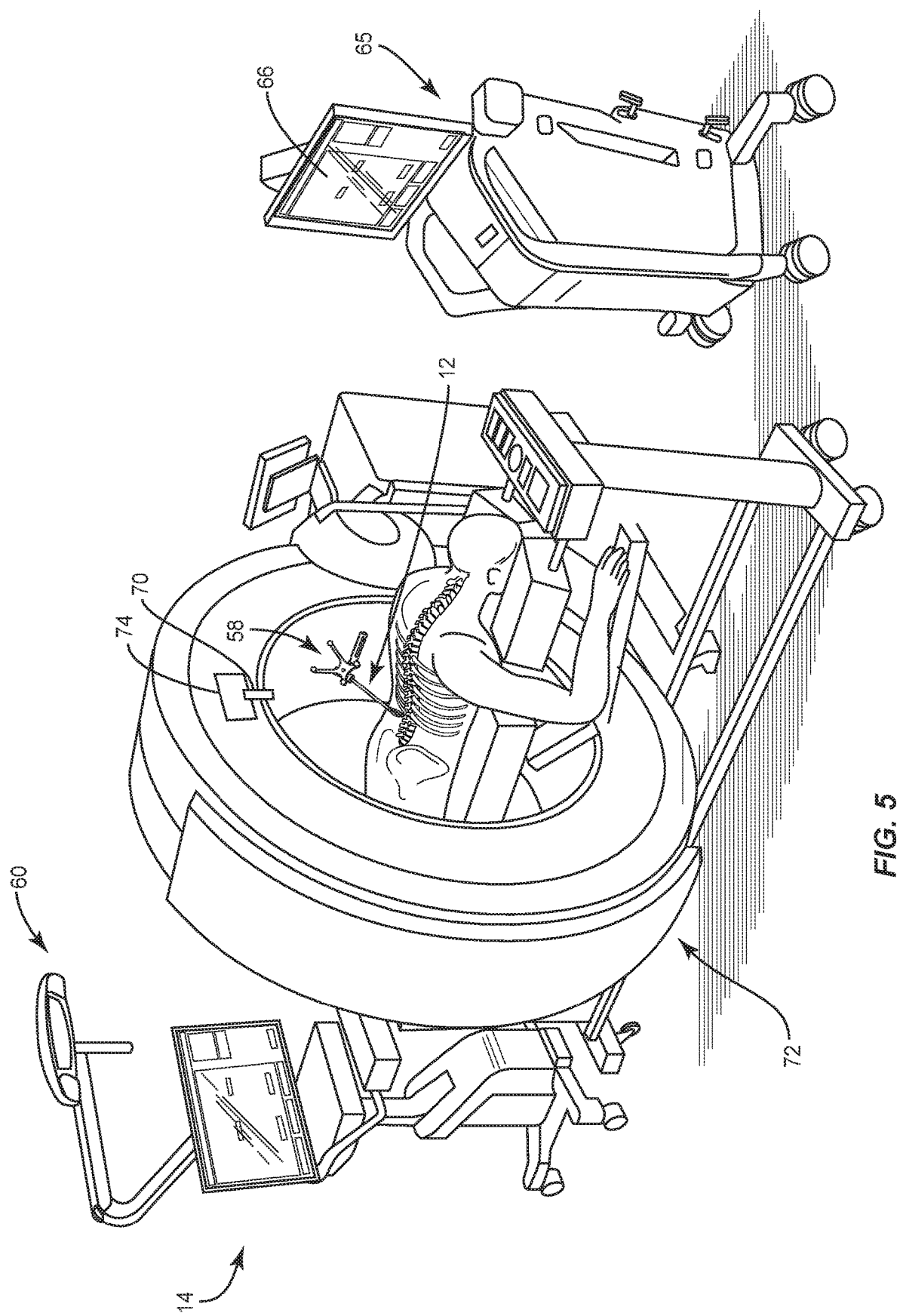
FIG. 5 is a perspective view of components of one embodiment of a surgical system in accordance with the principles of the present disclosure.

Trial instrument 12 is configured for disposal adjacent a surgical site such that navigation component 58 is oriented relative to a sensor array 60, as shown in FIG. 5, to facilitate communication between navigation component 58 and sensor array 60 during a surgical procedure, as described herein. Navigation component 58 is configured to generate a signal representative of a size, configuration and/or position of trial instrument 12 relative to a patient anatomy for generating an image of trial instrument 12 for display from monitor 66. In some embodiments, navigation component 58 is connected with trial instrument 12 via an integral connection, friction fit, pressure fit, interlocking engagement, mating engagement, dovetail connection, clips, barbs, tongue in groove, threaded, magnetic, key/keyslot and/or drill chuck.

Navigation component 58 includes an emitter array 62, as shown in FIG. 3. Emitter array 62 is configured for generating a signal to sensor array 60 of surgical navigation system 14. The signal generated by emitter array 62 includes data points that represent a size, configuration and/or position of one or more components of surgical system 10, for example, trial instrument 12 relative to a patient anatomy for generating an image of trial instrument 12 for display from monitor 66. In some embodiments, the signal generated by emitter array 62 includes data points that represent a three-dimensional position of trial instrument 12 relative to tissue for generating an image of trial instrument 12 for display from monitor 66. In some embodiments, emitter array 62 may include a reflector array configured to reflect a signal from sensor array 60.

Emitter array 62 includes four spaced apart arms having a substantially X-shape. Emitter array 62 includes markers, for example, fiducials 64. Fiducials 64 appear in the image produced by surgical navigation system 14 for use as a point of reference or a measure. Emitter array 62 generates signals representing the position of various reference points of the patient's anatomy. See, for example, similar surgical navigation components and their use as described in U.S. Pat. Nos. 6,021,343, 6,725,080, 6,796,988, the entire contents of each of these references being incorporated by reference herein. In some embodiments, fiducials 64 include at least one light emitting diode. In some embodiments, fiducials 64 may include other tracking devices capable of being tracked by sensor array 60, for example, a tracking device that actively generates acoustic signals, magnetic signals, electromagnetic signals, radiologic signals. In some embodiments, fiducials 64 may be removably attached to emitter array 62. In some embodiments, one or more of fiducials 64 each include a single ball-shaped marker.

In some embodiments, surgical navigation system 14 comprises image capturing portion 70 that may include an x-ray source or emission portion and an x-ray receiving or image receiving portion located generally or as practically possible 180 degrees from each other and mounted on a rotor (not shown) relative to a track of image capturing portion 70. Image capturing portion 70 can be operable to rotate 360 degrees during image acquisition. Image capturing portion 70 may rotate around a central point or axis, allowing image data of the patient to be acquired from multiple directions or in multiple planes. Surgical navigation system 14 can include those disclosed in U.S. Pat. Nos. 8,842,893, 7,188, 998; 7,108,421; 7,106,825; 7,001,045; and 6,940,941; the entire contents of each of these references being incorporated by reference herein.

In some embodiments, surgical navigation system 14 can include medical imaging, for example, C-arm fluoroscopic imaging systems, which can generate three-dimensional views of a patient. The position of image capturing portion 70 can be precisely known relative to any other portion of an imaging device of navigation system 14. In some embodiments, a precise knowledge of the position of image capturing portion 70 can be used in conjunction with a tracking system 72 to determine the position of image capturing portion 70 and the image data relative to the patient.

Tracking system 72 can include various portions that are associated or included with surgical navigation system 14. In some embodiments, tracking system 72 can also include a plurality of types of tracking systems, such as, for example, an optical tracking system that includes an optical localizer, such as, for example, sensor array 60 and/or an EM tracking system that can include an EM localizer. Various tracking devices can be tracked with tracking system 72 and the information can be used by surgical navigation system 14 to allow for a display of a position of an item, for example, a patient tracking device, an imaging device tracking device 74, and an instrument tracking device, for example, emitter array 62, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Sensor array 60 is located in such a manner to provide a clear line of sight with emitter array 62, as described herein. In some embodiments, fiducial markers 64 of emitter array 62 communicate with sensor array 60 via infrared technology. Sensor array 60 is coupled to computer 65, which may be programmed with software modules that analyze signals transmitted by sensor array 60 to determine the position of each object in a detector space.

For example, trial instrument 12, with emitter array 62 attached thereto as described herein, is selectively disposed with vertebral tissue according to an implant strategy. Trial instrument 12 can be manipulated in a vertebral space. Orientation of navigation component 58 relative to sensor array 60 facilitates communication between navigation component 58 and sensor array 60 during a surgical procedure, as described herein. Sensor array 60 receives signals from emitter array 62 to provide information including the data points, as described herein, regarding the size, configuration, spatial position and/or trajectory of trial instrument 12 relative to a portion of the patient's anatomy, as described herein. In some embodiments, surgical navigation system 14 provides for real-time tracking of trial instrument 12.

A processor of computer 65 executes one or more instructions in operation of surgical navigation system 14, as described herein, for generating imaging of one or more components of surgical system 10. Emitter array 62 generates a signal including the data points that represent size, configuration and/or a three-dimensional position of trial instrument 12 relative to the vertebral space. Emitter array 62 communicates the signal including the data points to the processor of computer 65. The processor measures, calibrates, samples, captures and/or identifies the size, configuration and/or three-dimensional position of trial instrument 12 in a three-dimensional space and generates an image of the data points of trial instrument 12 that represent size, configuration and/or three-dimensional position of trial instrument 12 for display from monitor 66, as described herein. See, for example, the surgical systems and methods described in U.S. Pat. No. 8,571,638, the contents of which being hereby incorporated by reference herein in its entirety. The processor of computer 65 is programed with known parameters of trial instrument 12, for example, a length of shaft 16 and body 18, a width of body 18. The processor utilizes the known parameters to calculate a position of body 18 relative to the vertebral space and creates an image of body 18 within tissue for display on monitor 66.

The three-dimensional image and position of trial instrument 12 including body 18 relative to vertebral tissue is saved to a database of computer 65. The three-dimensional image can be saved to the database for retrieval and/or maintained for display from monitor 66. The images of trial instrument 12 are transmitted to computer 65 for display on monitor 66, as well as, saved, digitally manipulated, or printed to a hard copy. In some embodiments, images may also be displayed to the surgeon through a heads-up display. Trial instrument 12 is removed from the vertebral space. The image of trial instrument 12 remains displayed on monitor 66.

Figure 16:
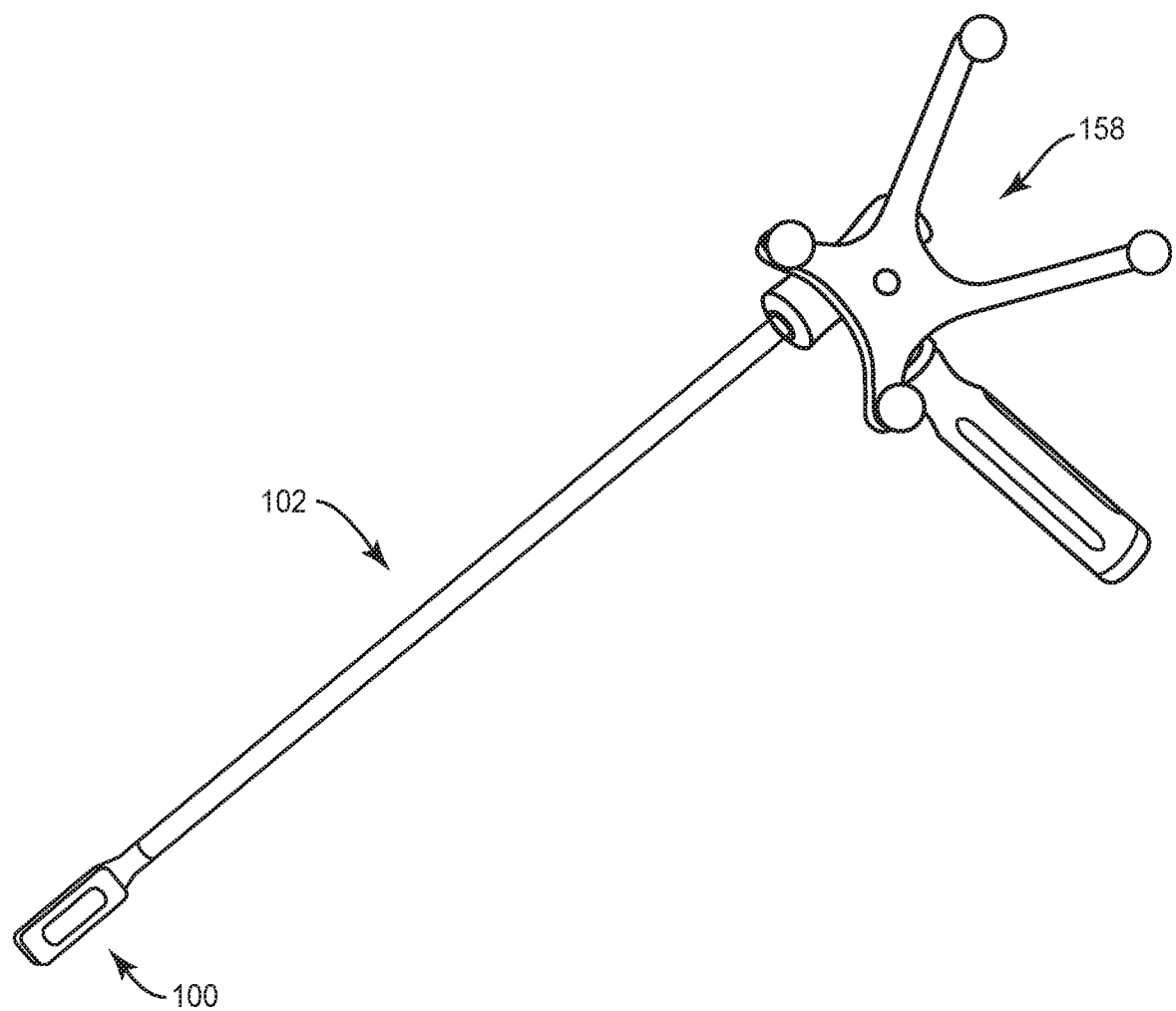
FIG. 16 is a side view of components of one embodiment of a surgical system in accordance with the principles of the present disclosure.

Spinal implant 100 is selected from a plurality of alternately sized and/or configured spinal implants according to the generated image of trial instrument 12. Spinal implant 100 is connected with an inserter 102, as shown in FIG. 16. Inserter 102 includes a navigation component 158, similar to navigation component 58, as described herein. In some embodiments, inserter 102 includes an expandable surgical driver configured to expand an expandable spinal implant. Spinal implant 100 is introduced into the vertebral space. Navigation component 158 communicates a signal including data points of spinal implant 100 to the processor of computer 65 to measure, calibrate, sample, capture and/or identify the size, configuration and/or position of spinal implant 100 in a three-dimensional space for display and real time tracking of an image of the data points that represent a three-dimensional image including size, configuration and/or position of spinal implant 100 for display from monitor 66, as described herein. The image of spinal implant 100 is generated relative to the image of trial instrument 12 displayed from monitor 66. Spinal implant 100 is guided and/or aligned with the image of trial instrument 12 for accurate positioning of spinal implant 100 in accordance with an implant strategy.

In assembly, operation and use, surgical system 10, similar to the systems and methods described herein, is employed with a surgical procedure, for treatment of a spine of a patient including vertebrae V. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 4:
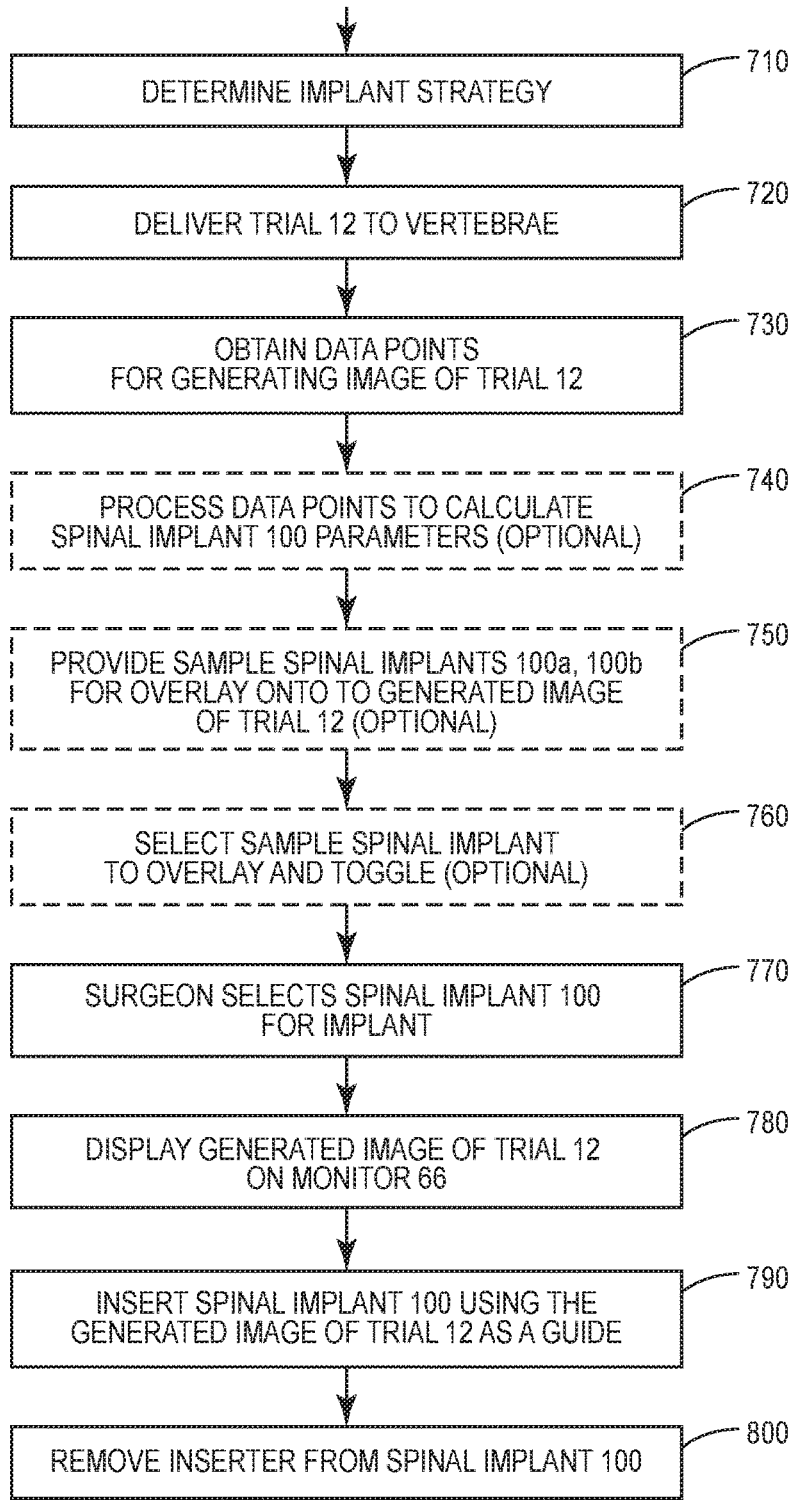
FIG. 4 is a flow diagram illustrating representative steps of embodiments of a method and a surgical system in accordance with the principles of the present disclosure.
Figure 6:
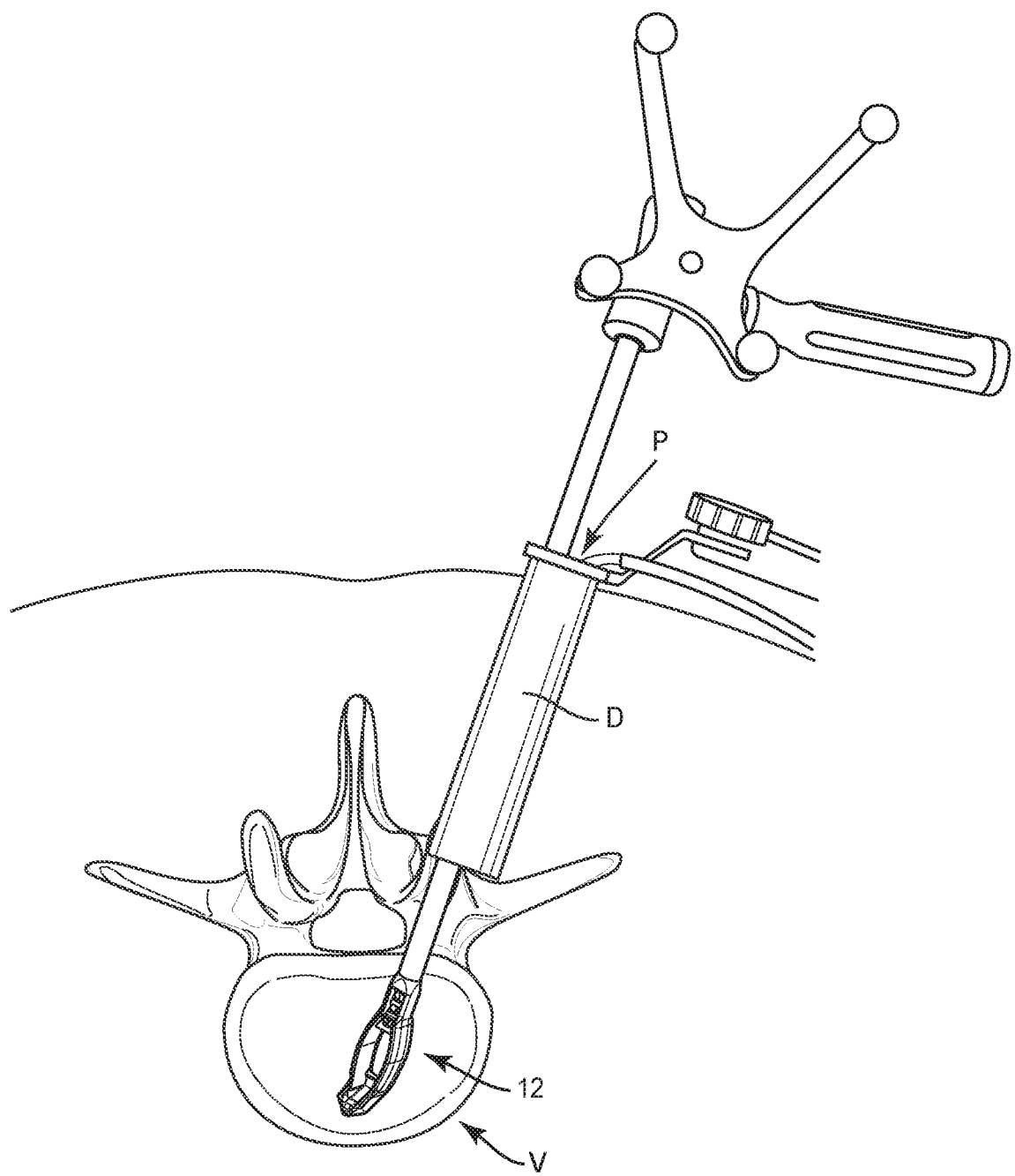
FIG. 6 is an axial view of components of one embodiment of a surgical system in accordance with the principles of the present disclosure disposed with patient anatomy.
Figure 7:
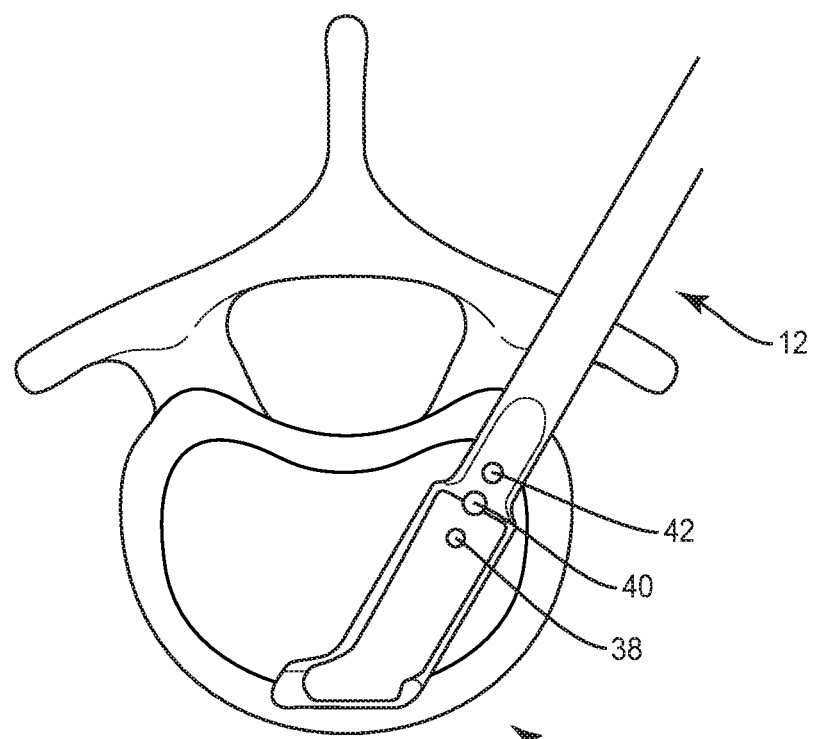
FIG. 7 is a graphical representation of a computer display of components of one embodiment of a surgical system in accordance with the principles of the present disclosure disposed with vertebrae.
Figure 8:
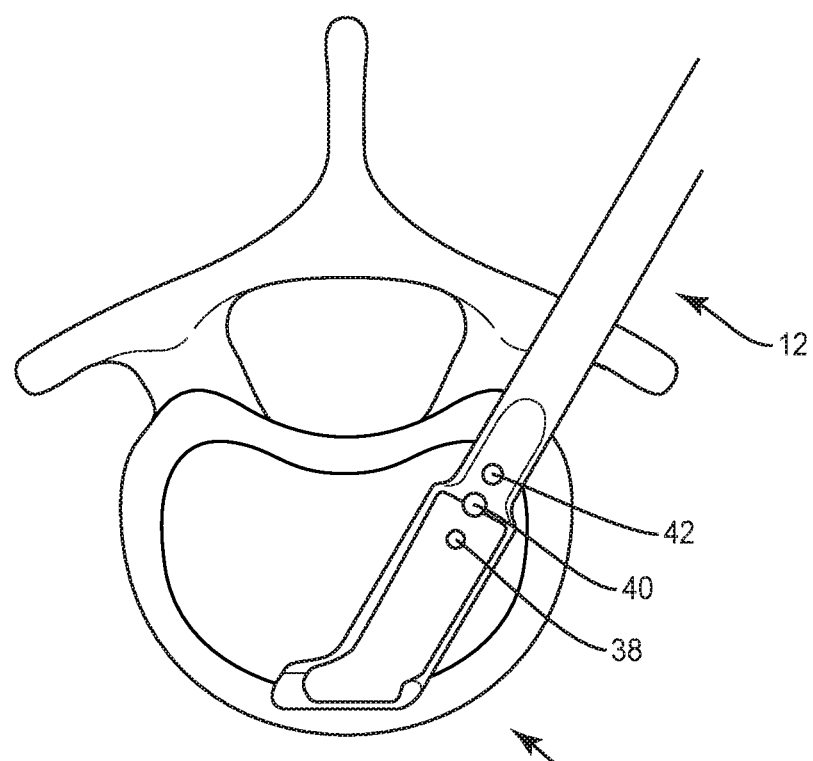
FIG. 8 is a graphical representation of a computer display of components of one embodiment of a surgical system in accordance with the principles of the present disclosure disposed with vertebrae.
Figure 9:
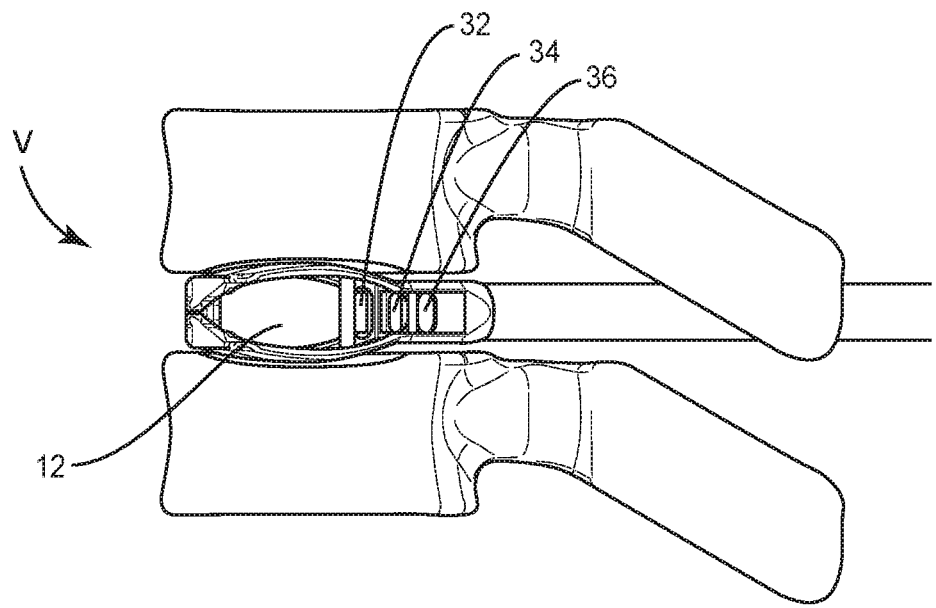
FIG. 9 is a side view of components of one embodiment of a surgical system in accordance with the principles of the present disclosure disposed with vertebrae.
Figure 10:
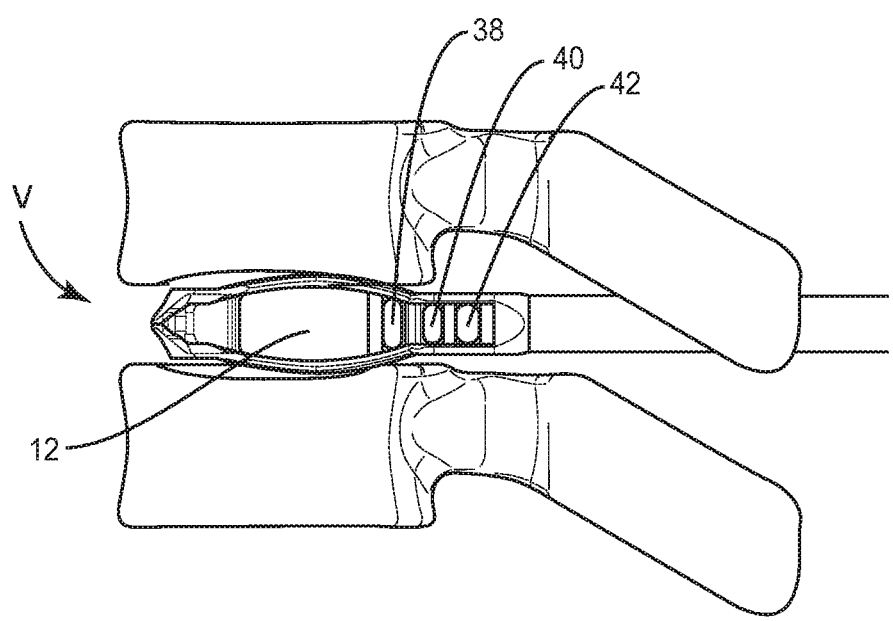
FIG. 10 is a side view of the components and vertebrae shown in FIG. 9.

In one embodiment, as shown in FIG. 4, surgical system 10, similar to the systems and methods described herein, is employed in connection with one or more surgical procedures. During a surgery 700, an implant strategy is determined, in a step 710. For example, a surgeon reviews three-dimensional scans of the patient and formulates and selects an implant strategy for the components of a spinal construct with the patient anatomy according to the three-dimensional scan. In some embodiments, the implant strategy includes preparing a pre-operative surgical plan based on the three-dimensional scan. In some embodiments, the implant strategy includes selecting a surgical pathway P, for example, for insertion of the components of surgical system 10 into a lateral portion of vertebral tissue, as shown in FIG. 6. In some embodiments, the implant strategy employs pre-operative analytics software including anatomy recognition and vertebral segmentation algorithms for surgical visualization based on a patient's images, which facilitates formulating the implant strategy including implant and trajectory placement planning. In some embodiments, the implant strategy may be created pre-operatively or intra-operatively.

Trial instrument 12, as described herein, is selected according to the implant strategy. In a step 720, trial instrument 12 is delivered along surgical pathway P through dilator D for disposal with a lateral portion of vertebrae V, as shown in FIGS. 6-10. Trial instrument 12 distracts one or more intervertebral spaces and applies appropriate tension in the intervertebral space allowing for indirect decompression. Trial instrument 12 is adjusted and/or various sizes of trial instruments 12 may be inserted.

Figures 11, 12:
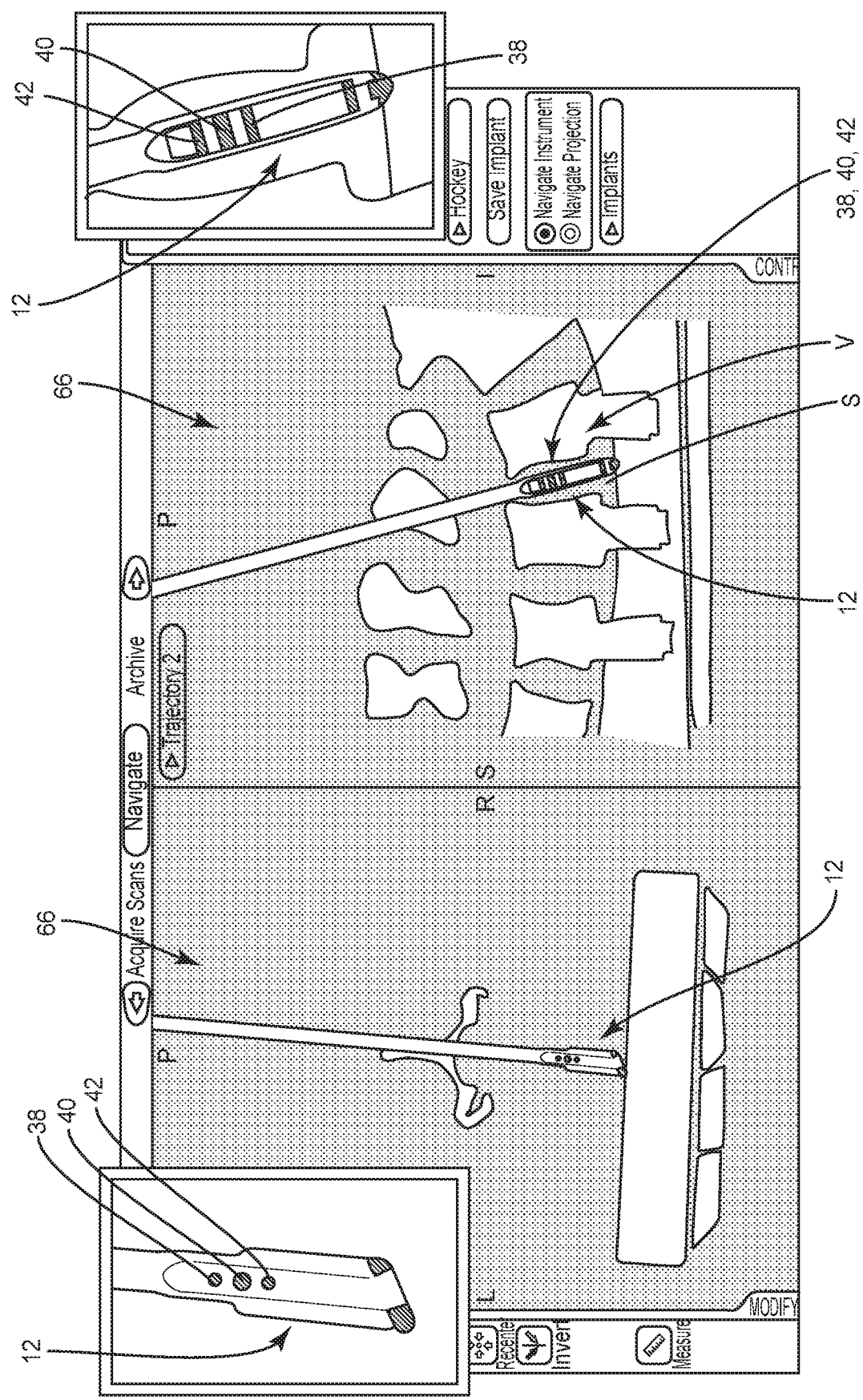
FIG. 11 is a graphical representation of a computer display of components of one embodiment of a surgical system in accordance with the principles of the present disclosure disposed with vertebrae.
FIG. 12 is a graphical representation of a computer display of components of one embodiment of a surgical system in accordance with the principles of the present disclosure disposed with vertebrae.

In a step 730, an image of trial instrument 12 is generated by measuring, sampling, capturing and/or identifying size, configuration and/or positional data points of trial instrument 12 relative to vertebrae V for display from computer monitor 66, as described herein. The generated image of trial instrument 12 including markers 30 is graphically displayed on monitor 66, as shown in FIGS. 11 and 12.

In some embodiments, in an optional step 740, the processor of computer 65 calculates parameters for the shape, height and length of spinal implant 100 to be implanted. In some embodiments, in an optional step 750, the processor provides model spinal implants, for example, spinal implants 100a, 100b, on a graphical user interface including a drop-down menu, as shown in FIG. 13. Spinal implants 100a, 100b can vary by material, length, width, height, configuration and/or the procedure to be utilized. For example, the configuration of spinal implants 100a, 100b may be straight, curved, bullet nose, dolphin nose, and/or hockey stick shaped.

In some embodiments, an image of spinal implants 100a, 100b selected from the dropdown menu can be overlaid on the generated image of trial instrument 12 to compare the configuration, size, height and/or length of the overlay image to the generated image of trial instrument 12. In an optional step 760, a surgeon enters a selection of one of spinal implants 100a, 100b from the drop-down menu, for example, spinal implant 100a. The image of spinal implant 100a is oriented for overlay relative to the generated image of trial instrument 12, as shown in FIGS. 14 and 15.

In some embodiments, the surgeon can toggle between spinal implants 100a, 100b provided on the drop-down menu to determine which spinal implant 100a, 100b is optimal based on the comparison with the generated image of trial instrument 12. In some embodiments, the graphical user interface allows for adjusting the configuration, size and/or length of the overlay image of spinal implant 100a relative to the generated image of trial instrument 12 and/or patient anatomy. In some embodiments, the generated image of trial instrument 12 and the overlay image of spinal implant 100a is generated and saved on computer 65. The generated image of trial instrument 12 with overlay of spinal implant 100a is utilized to guide and/or align insertion of a selected spinal implant 100, as described herein.

Figure 17:
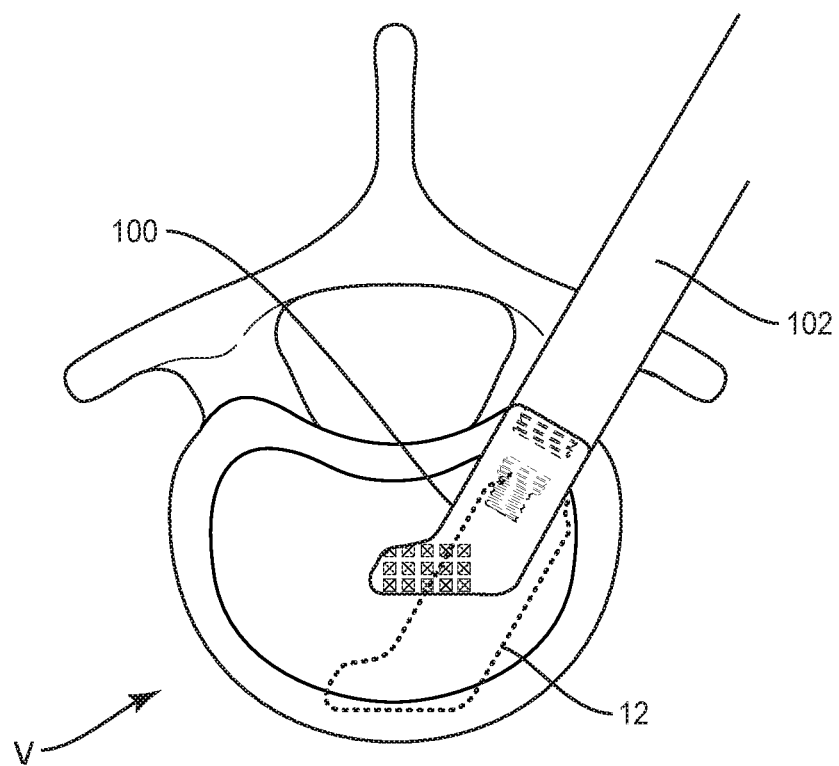
FIG. 17 is a graphical representation of a computer display of components of one embodiment of a surgical system in accordance with the principles of the present disclosure disposed with vertebrae.
Figure 18:
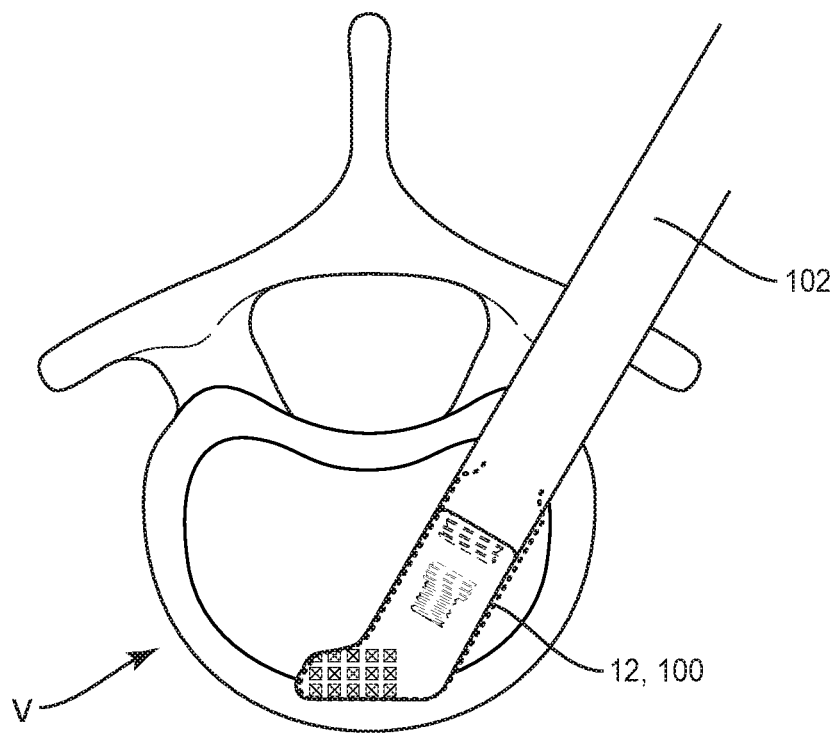
FIG. 18 is a graphical representation of a computer display of components of one embodiment of a surgical system in accordance with the principles of the present disclosure disposed with vertebrae.
Figure 19:
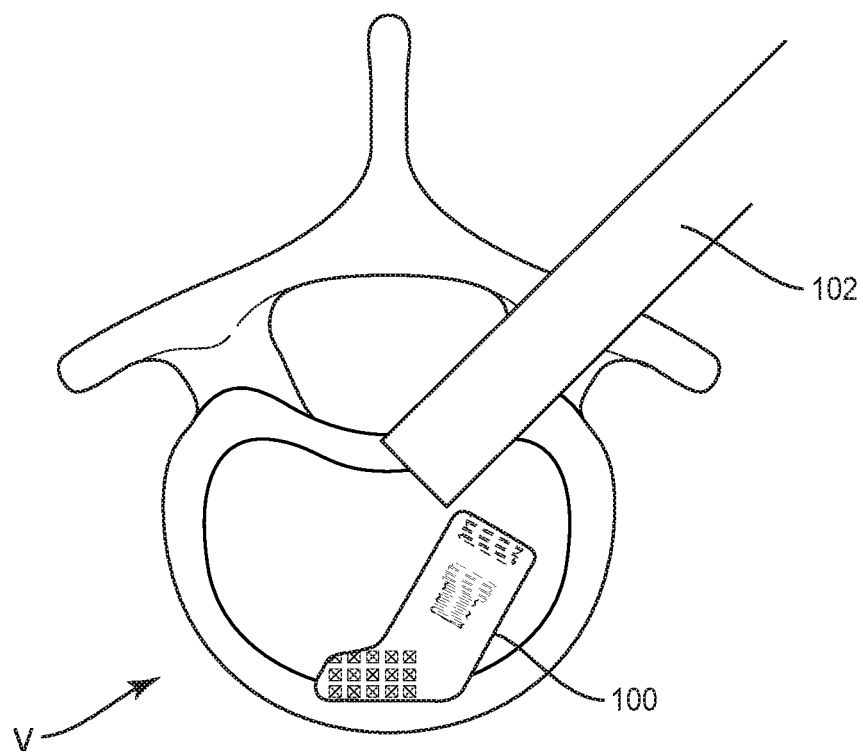
FIG. 19 is a graphical representation of a computer display of components of one embodiment of a surgical system in accordance with the principles of the present disclosure disposed with vertebrae.
Figure 20:
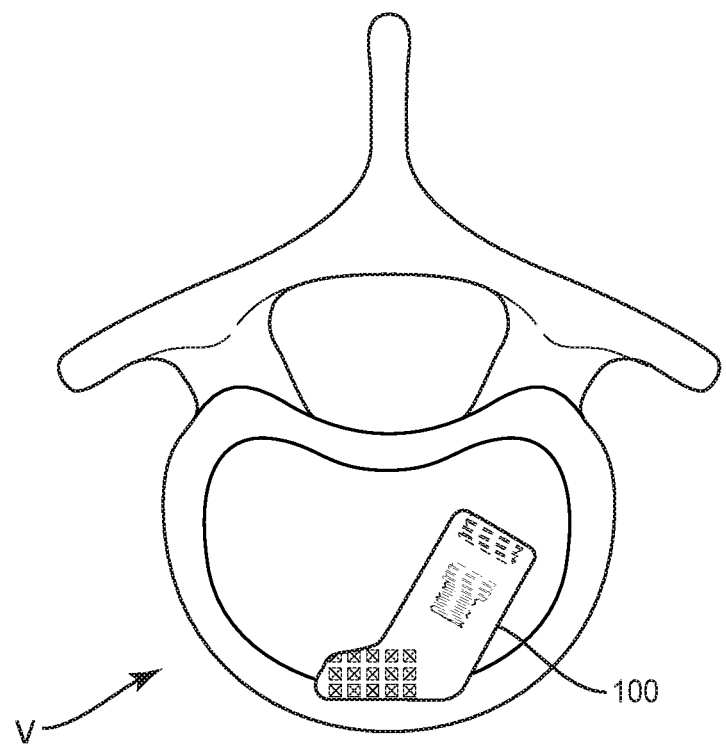
FIG. 20 is a graphical representation of a computer display of components of one embodiment of a surgical system in accordance with the principles of the present disclosure disposed with vertebrae.
Figure 21:
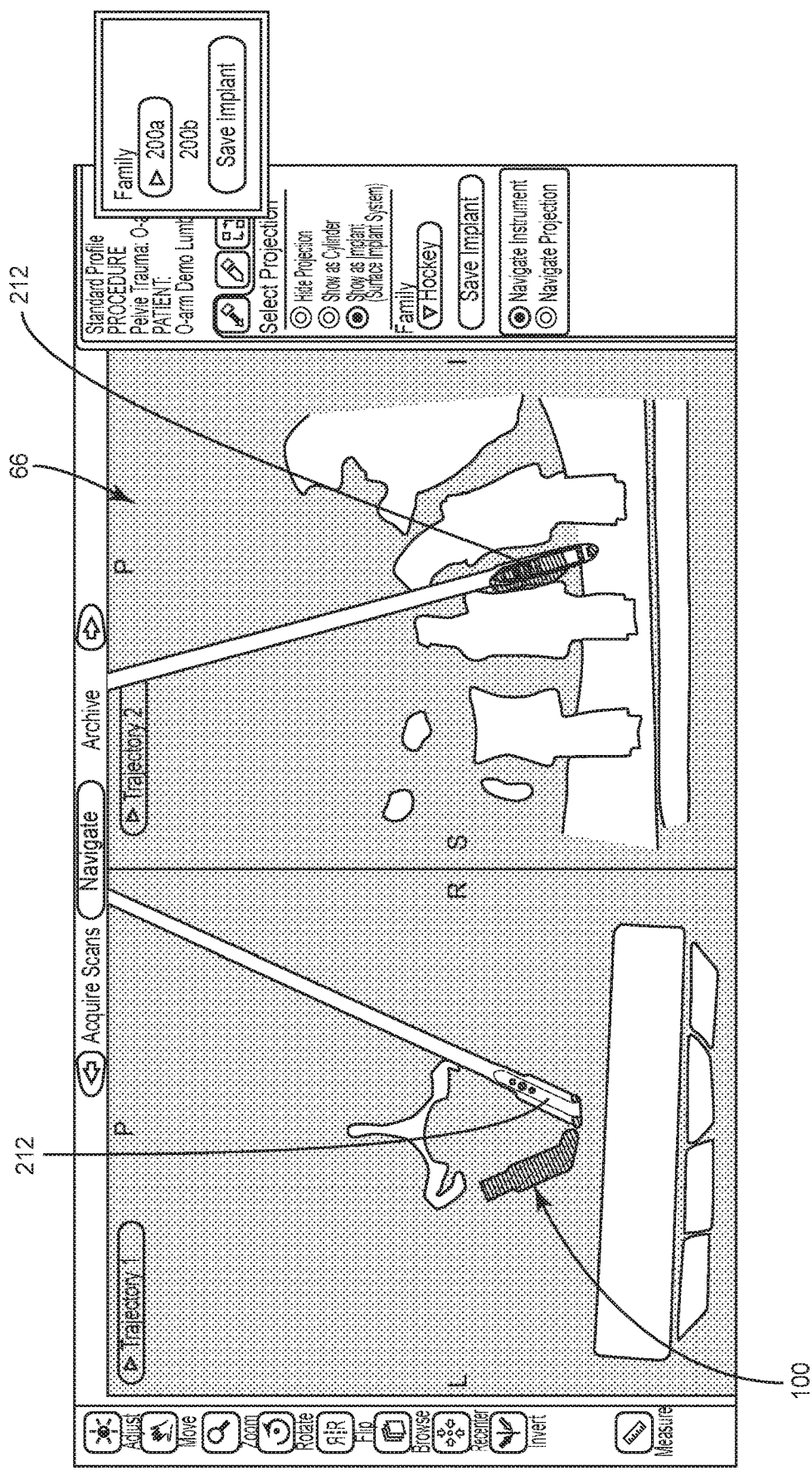
FIG. 21 is a graphical representation of a computer display of components of one embodiment of a surgical system in accordance with the principles of the present disclosure disposed with vertebrae.
Figure 22:
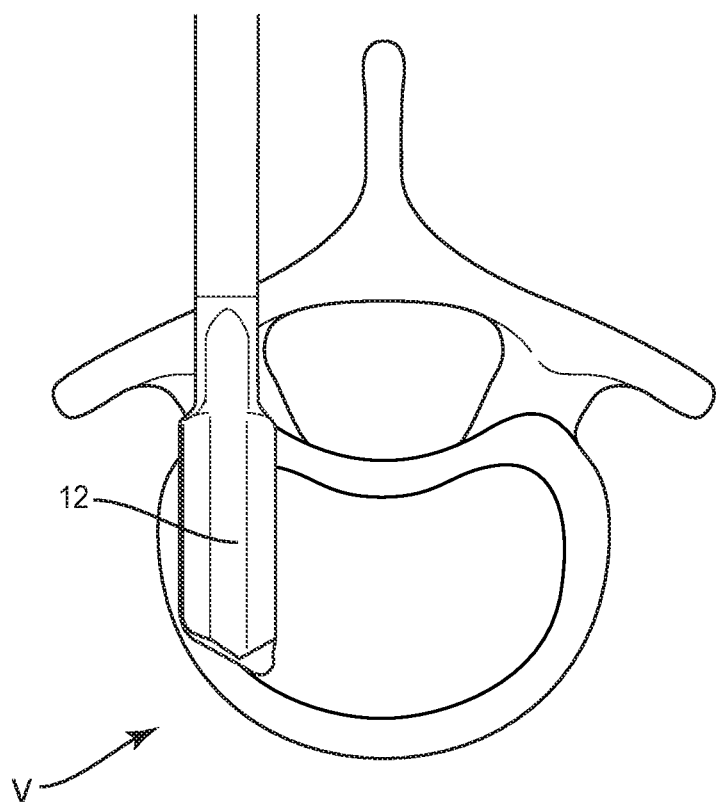
FIG. 22 is a graphical representation of a computer display of components of one embodiment of a surgical system in accordance with the principles of the present disclosure disposed with vertebrae.
Figure 23:
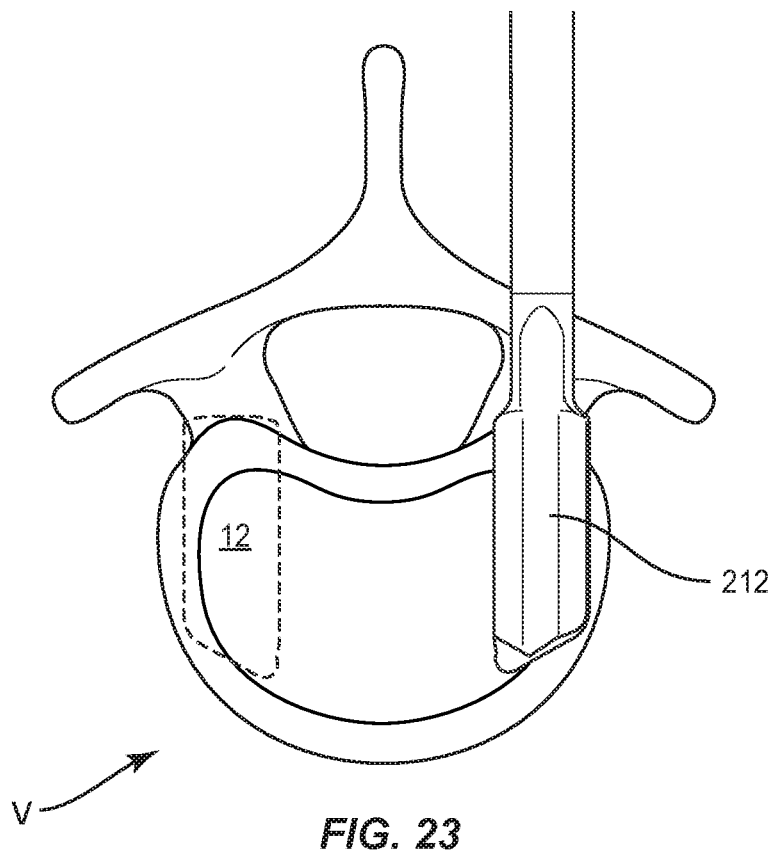
FIG. 23 is a graphical representation of a computer display of components of one embodiment of a surgical system in accordance with the principles of the present disclosure disposed with vertebrae.
Figure 24:
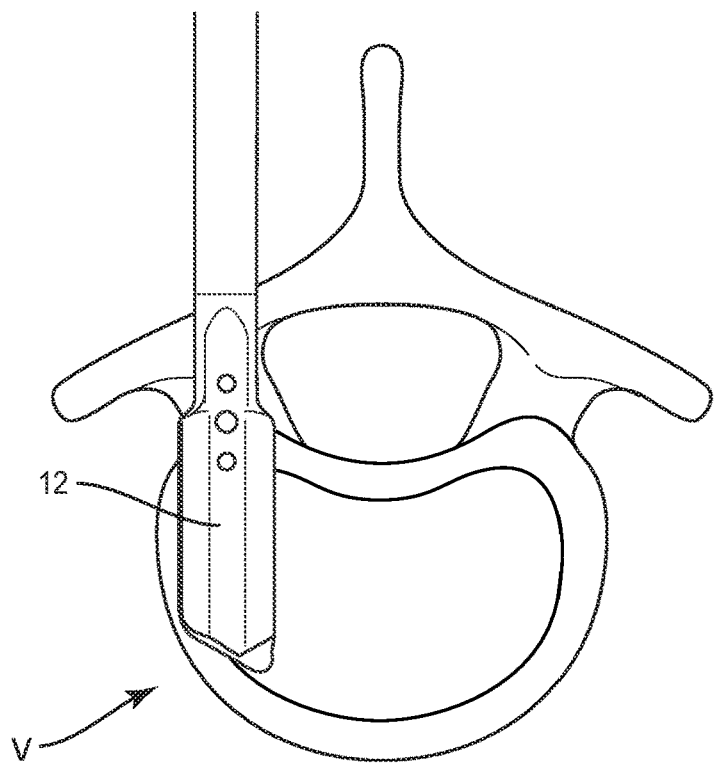
FIG. 24 is a graphical representation of a computer display of components of one embodiment of a surgical system in accordance with the principles of the present disclosure disposed with vertebrae.

Trial instrument 12 is removed. In a step 770, a spinal implant 100 is selected according to the implant strategy. Spinal implant 100 is connected with an inserter 102, as described herein. In a step 780, the generated image of trial instrument 12 is retrieved and displayed on monitor 66. In some embodiments, the generated image of trial instrument 12 remains on monitor 66 from step 730. In a step 790, spinal implant 100 is inserted along surgical pathway P, as shown in FIGS. 17-20. An image of spinal implant 100 is generated by measuring, sampling, capturing and/or identifying size, configuration and/or positional data points of spinal implant 100 relative to vertebral tissue for display from computer monitor 66, as described herein. The image of spinal implant 100 is generated relative to the image of trial instrument 12 displayed from monitor 66. The generated image of trial instrument 12 is utilized to guide and/or properly align spinal implant 100 within vertebral space S, as shown in FIGS. 17 and 18. In some embodiments, monitor 66 may indicate when spinal implant 100 is properly aligned with the generated image of trial instrument 12 to alert the surgeon. For example, the generated image of trial instrument 12 may illuminate, change color, red, blue or green, and/or a border around the display window illuminates or changes color or indicates a home position, when spinal implant 100 is aligned and/or sufficiently overlapped with the generated image of trial instrument 12. In a step 800, once spinal implant 100 is aligned, inserter 102 is disengaged from spinal implant 100 and removed, as shown in FIGS. 19 and 20. In some embodiments, one or more steps or portions of a surgical procedure may be performed without the use of pre-operative analytics software, a generated image of a trial instrument and/or a generated image of a spinal implant.

In some embodiments, a surgical procedure, similar to that described herein, includes insertion of spinal implant 100 with a lateral portion of vertebrae V, as described herein, and a spinal implant 200 inserted with a contra-lateral portion of vertebrae V, as shown in FIGS. 21-25. In some embodiments, the implant strategy includes selecting one or more surgical pathways P for positioning a plurality of spinal implants 100, 200 with vertebrae V. Trial instrument 12 and spinal implant 100 are inserted, as described herein. A trial instrument 212 is inserted with vertebrae V and an image of trial instrument 212 relative to vertebrae V is generated, as described herein. The generated image of trial instrument 212 is stored in computer 65 for display on monitor 66, as described herein. Trial instrument 212 is removed.

Figure 25:
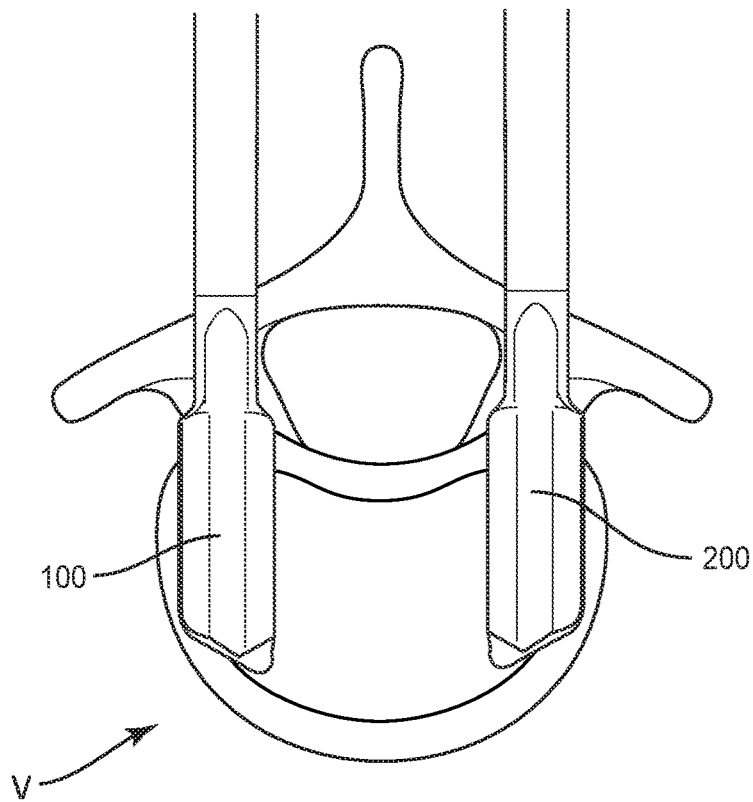
FIG. 25 is a graphical representation of a computer display of components of one embodiment of a surgical system in accordance with the principles of the present disclosure disposed with vertebrae.

A selected spinal implant 200 is connected with an inserter, as described herein, and is disposed with vertebrae V. Real time tracking of spinal implant 200 is captured and displayed on monitor 66 relative to the image of trial instrument 212, an image of spinal implant 100 as described herein, and/or an image of trial instrument 12 as described herein, to simultaneously track one or more components of surgical system 10, for example, instruments and/or implants. The image of spinal implant 200 is generated relative to the images and vertebrae V displayed from monitor 66. The generated images of trial instrument 212, spinal implant 100 and/or trial instrument 12, are utilized to guide and/or align spinal implant 200 within vertebral space S. Once spinal implant 200 is selectively aligned with vertebrae V, the inserter is disengaged from spinal implant 200 and removed. Spinal implants 100, 200 remain with vertebrae V, as shown in FIG. 25.

In some embodiments, the surgical procedure requires that trial instruments 12, 212 remain within vertebral space S to maintain distraction of vertebrae V during insertion of spinal implants 100, 200. For example, navigation components 58, 158 may be removed from trial instruments 12, 212 and trial instruments 12, 212 remain within vertebral space S. As such, trial instruments 12, 212 are no longer viewable on monitor 66. The surgeon can retrieve the saved generated images of trial instruments 12, 212 to facilitate insertion, guidance and positioning of spinal implants 100, 200 with the vertebral tissue, as described herein.

Upon completion of one or more surgical procedures, the surgical instruments and non-implanted components of surgical system 10 are removed and the incision(s) are closed. One or more of the components of surgical system 10 can be made of radiolucent materials such as polymers. In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
    a trial connected with a first image guide oriented relative to a sensor to communicate a signal representative of the trial relative to a patient anatomy;
    a tracking device including the sensor and communicating with a processor to generate a storable image of the trial relative to the patient anatomy for display on a monitor; and
    a spinal implant connected with a second image guide oriented relative to the sensor to communicate a signal representative of the spinal implant relative to the patient anatomy, the sensor receiving the signal of the second image guide and communicating with the processor to generate an image of the spinal implant in real time for display on the monitor such that the image of the spinal implant overlays the image of the trial to align the spinal implant in real time with the stored image of the trial.

2. A surgical system as recited in claim 1, wherein a size and/or configuration of the image of the trial is adjustable via the display from the monitor.

3. A surgical system as recited in claim 2, wherein the display includes a graphical user interface for adjusting the size and/or configuration of the image of the trial.

4. A surgical system as recited in claim 1, wherein the trial includes indicia displayable from the monitor to represent orientation of the trial relative to the patient anatomy.

5. A surgical system as recited in claim 4, wherein the indicia includes one or more radiopaque markers disposed adjacent a distal end of the trial.

6. A surgical system as recited in claim 1, wherein the trial includes indicia displayable from the monitor to represent a size of the spinal implant.

7. A surgical system as recited in claim 6, wherein the indicia includes axial indicia.

8. A surgical system as recited in claim 6, wherein the indicia includes one or more fins.

9. A surgical system as recited in claim 6, wherein the indicia includes one or more axial oriented columns.

10. A surgical system as recited in claim 9, wherein the columns include a distal column, an intermediate column and a proximal column, the intermediate column having a diameter different than a diameter of the distal column and a diameter of the proximal column.

11. A surgical system as recited in claim 6, wherein the indicia includes lateral indicia.

12. A surgical system as recited in claim 6, wherein the indicia includes an axial indicia and a lateral indicia.

13. A surgical system as recited in claim 1, wherein the processor generates an alternate trial image having an alternate size and/or configuration relative to the image of the trial for display from the monitor with the image of the trial.

14. A surgical system as recited in claim 1, wherein the spinal implant is selected from a plurality of alternately sized and/or configured spinal implants according to the image of the trial.

15. A system comprising:
  a tangible storage device comprising computer-readable instructions;
  an image guide being oriented relative to a sensor for positional tracking of one or more trials, one or more spinal implants and/or a patient anatomy; and
  a processor, executing the instructions in operation of the system for:
  imaging at least one trial with the patient anatomy;
  acquiring data points representative of an image of the at least one trial selectively positioned relative to the patient anatomy;
  displaying the image on a computer monitor;
  imaging at least one spinal implant with the patient anatomy to generate an image of the at least one spinal implant;
  overlaying the image of the at least one spinal implant onto the image of the at least one trial on the computer monitor; and
  aligning the image of the at least one spinal implant with the image of the at least one trial.

16. A surgical system as recited in claim 15, wherein a size and/or configuration of an image of the at least one trial is adjustable via the display from the computer monitor.

17. A surgical system as recited in claim 16, wherein the display includes a graphical user interface for adjusting the size and/or configuration of the image of the trial.

18. A surgical system as recited in claim 15, wherein the at least one trial includes indicia displayable from the computer monitor to represent orientation of the at least one trial relative to the patient anatomy.

19. A surgical system comprising:
  a trial connected with a first image guide oriented relative to a sensor to communicate a signal representative of the trial relative to a patient anatomy;
  a tracking device including the sensor and communicating with a processor to generate a storable image of the trial relative to the patient anatomy for display from a monitor; and
  a spinal implant connected with a second image guide oriented relative to the sensor to communicate a signal representative of the spinal implant relative to the patient anatomy, the sensor receiving the signal of the second image guide and communicating with the processor to generate an image of the spinal implant in real time for display from the monitor in a configuration to align the spinal implant in real time with the stored image of the trial,
  wherein the trial includes indicia displayable from the monitor to represent a size of the spinal implant,
  wherein the indicia includes one or more axial oriented columns, and
  wherein the columns include a distal column, an intermediate column and a proximal column, the intermediate column having a diameter different than a diameter of the distal column and a diameter of the proximal column.

20. A surgical system as recited in claim 19, wherein the processor generates an alternate trial image having an alternate size and/or configuration relative to the image of the trial for display from the monitor with the image of the trial.

* * * * *